(12) United States Patent
Wesolowski et al.

(10) Patent No.: US 8,738,345 B2
(45) Date of Patent: May 27, 2014

(54) METHOD FOR EVALUATING RENAL FUNCTION

(75) Inventors: Carl A. Wesolowski, St. John's (CA); Paul Babyn, Caledon (CA); Richard Puetter, San Diego, CA (US)

(73) Assignee: Carl A. Wesolowski, St. John's, Newfoundland & Labrador (CA)

( * ) Notice: Subject to any disclaimer, the term of this patent is extended or adjusted under 35 U.S.C. 154(b) by 18 days.

(21) Appl. No.: 13/375,213

(22) PCT Filed: Jun. 1, 2010

(86) PCT No.: PCT/US2010/036924
§ 371 (c)(1),
(2), (4) Date: Feb. 3, 2012

(87) PCT Pub. No.: WO2010/138967
PCT Pub. Date: Dec. 2, 2010

(65) Prior Publication Data
US 2012/0123694 A1 May 17, 2012

Related U.S. Application Data

(60) Provisional application No. 61/182,676, filed on May 29, 2009.

(51) Int. Cl.
*G06G 7/48* (2006.01)
*G01N 1/00* (2006.01)
*G06T 1/00* (2006.01)

(52) U.S. Cl.
CPC ... *G01N 1/00* (2013.01); *G06T 1/00* (2013.01)
USPC .......................................................... 703/11

(58) Field of Classification Search
None
See application file for complete search history.

(56) References Cited

U.S. PATENT DOCUMENTS

| 5,500,372 A | 3/1996 | Kell |
| 6,647,358 B2 | 11/2003 | Grass et al. |
| 7,085,690 B2 | 8/2006 | Sale |

OTHER PUBLICATIONS

Davenport et al. (J. Nucl. Med. 24: 945-948, 1983).*
Stevens L.A. et al. Assessing kidney function: Measured and estimated glomerular filtration rate, New England Journal of Medicine, 2006, vol. 354, pp. 2473-2483.
Hermoye L. et al. Calculation of the renal perfusion and glomerular filtration rate from the renal impulse response obtained with MRI. Magnetic Resonance in Medicine, May 2004, vol. 51, No. 5, pp. 1017-1025.
Daghini E et al. Comparison of mathematic models for assessment of glomerular filtration rate with electron-beam CT in pigs. Radiology, Feb. 2007, vol. 242, No. 2, pp. 417-424.
Koh T.S. & Hous Z. A numerical method for estimating blood flow by dynamic functional imaging. Medical Engineering & Physics, 2002, vol. 24, pp. 151-158.
Calamante F et al. Quantification of bolus-tracking MRI: improved characterization of the tissue residue function using Tikhonov regularization. Magnetic Resonance in Medicine, Dec. 2003, vol. 50, No. 6, pp. 1237-1247.
International Search Report and Written Opinion issued Feb. 22, 2011 for PCT/US2010/036924, 10 pages.
Tolle K.M. et al., Estimating drug/plasma concentration levels by applying neural networks to pharmacokinetic data sets. Decision Support Systems, 2000, vol. 30, pp. 139-151.
Russell, C.D., et al, Measurement of Glomerular Filtration Rate: Single Injection of Plasma Clearance Method Without Urine Collection. J Nucl Med, 1985, vol. 26, pp. 1243-1247.
Brater, D. C., Measurement of renal function during drug development. J Clin Pharmacol, 2002, vol. 54, pp. 87-95.
Wesolowski, C.A., et al., Validation of Tikhonov adaptively regularized gamma variate fitting with 24-h plasma clearance in cirrhotic patients with ascites. Eur J Nucl Med Mol Imaging, Dec. 2011; vol. 38, No. 12, pp. 2247-2256; Epub: Sep. 1, 2011.
Wesolowski, C.A., et al., Tikhonov adaptively regularized gamma variate fitting to assess plasma clearance of inert renal markers, J Pharmacokinet Pharmacodyn, Oct. 2010, vol. 37, No. 5, pp. 435-474; Epub Sep. 24, 2010.
Wesolowski, C.A., et al., An improved method for determining renal sufficiency using volume of distribution and weight from bolus 99mTc-DTPA, two blood sample, paediatric data. Nucl Med Commun., Dec. 2006; vol. 27, No. 12, pp. 963-970.
Calvert, A.H.,. et al. Cadoblatin dosing formulae: gender bias and the use of creatinine-based methodologies, European Journal of Cancer 2002, vol. 38, pp. 11-16.
Gall P. et al., Extraction of the first bolus passage in dynamic susceptibility contrast perfusion measurements; Magn Reson Mater Phys 2009 22:241-249.
Levitt, D., The pharmacokinetics of the interstitial space in humans. BMC Clinical Pharmacology, 2003, 3:3, 29 pages.
Medeiros, F.S.R., et al., Validation of plasma clearance of 51Cr-EDTA in adult renal transplant recipients: comparison with inulin renal clearance, Transplant International, vol. 22, pp. 323-331, 2008.
Heiene, R. and Moe, L., Pharmacokinetic Aspects of Measurement of Glomerular Filtration Rate in the Dog: A Review, J Vet Intern Med., 1998, vol. 12, pp. 401-414.
Zanderigo, F. et al., Nonlinear Stochastic Regularization to Characterize Tissue Residue Function in Bolus-Tracking MRI: Assessment and Comparison With SVD, Block-Circulant SVD, and Tikhonov, IEEE Trans. on Biomedical Engineering, May 2009, vol. 56, pp. 1287-1297.
Supplementary European Search Report and Annex, European Patent Office, Completed Oct. 12, 2012, pp. 1-11.

* cited by examiner (Continued)

*Primary Examiner* — Pablo S Whaley
(74) *Attorney, Agent, or Firm* — Eleanor M. Musick; Procopio, Cory, Hargreaves & Savitch LLP

(57) ABSTRACT

Plasma concentration of a compound of interest is measured in two or ideally 4 or more blood samples taken from a patient over a period of time following bolus injection. The measured values are input into a computer processor programmed to execute a computer program comprising an algorithm that uses the gamma variate (GV) function to model drug plasma concentration, then uses Tikhonov regularization to perform the fit, selecting a regularization constant so that the relative error in the plasma clearance is minimized. One or more output values representative of renal function are generated.

15 Claims, 6 Drawing Sheets

METHOD FOR EVALUATING RENAL FUNCTION

FIELD OF THE INVENTION

The present invention relates to a method for measuring the rate of renal elimination of drugs or other compounds from the blood.

BACKGROUND OF THE INVENTION

Renal elimination is the single most important route of elimination of many metabolites and drugs in the body. For patients with decreased renal function, doses need to be decreased to avoid exposure to excessive drug concentrations that may cause toxicity. Renal plasma clearance (CL) measurements are indicated for evaluating renal function, controlling dosing and avoiding toxicity, and for transplant donor and recipient evaluation, amongst other indications.

There are several mechanisms of renal elimination, the first being glomerular filtration. This is a passive mechanism of elimination, whereby ionic substances are renally filtered and excreted. A gold standard test for measuring glomerular filtration rate or plasma clearance is the inulin constant infusion assay. This test, and other constant infusion assays, involves infusion of inulin or other test compound at a constant rate followed by measurement of its concentration in urine and/or plasma over time. Inulin is completely filtered at the glomerulus and is neither secreted nor reabsorbed by the renal tubules. However, inulin constant infusion may not be useful in patients with severely reduced renal function. Moreover, inulin constant infusion testing has been twice reported to cause anaphylactic shock in humans, and other, safer substances and more generally applicable methods are needed for CL estimation. Another gold standard performs a numerical integration of the area under the curve (AUC) for 24 hours or more after bolus (i.e., sudden) injection of a test substance. Gold standard tests have the advantages of accuracy and robustness because they do not require extensive use of curve fitting. Unfortunately, the repeated sampling over extended periods of time makes the numerical integration of AUC impractical, particularly in a clinical setting, and even 24 hour collections may not be long enough to evaluate renal failure A second mechanism of renal elimination is tubular secretion, which can increase the CL by actively secreting the drug, as opposed to only the passive diffusion in glomerular filtration. The rate of secretion depends on the transporter. Compounds that are secreted usually also undergo glomerular filtration, so renal clearance is the sum of both routes.

A third mechanism affecting the renal clearance of drugs is tubular reabsorption. Some drugs may be reabsorbed after being filtered out of the blood. Thus, the CL may be smaller than expected (when considering only filtration and tubular secretion.) If a drug is "completely" reabsorbed after filtration and no active secretion takes place, the renal clearance will be limited to the amount of drug that leaves the kidney as the urine flows into the bladder. Because of these additional mechanisms, glomerular filtration rate alone using one of the gold standards may not always accurately model CL for some drugs or metabolites.

As a result of the various drawbacks of the gold standard tests, the more common approach to estimating CL is to use curve fitting models. Such models include Sums of Exponential Terms, or SETs, and Gamma Variate (GV). Examples of SETs include ordinary least squares (OLS) regression, Bayesian priors, D-optimal design and Tikhonov regularization (Tk-SET). An example of GV is OLS GV regression. To test how good a curve fit model is, one must test (a) whether one curve fit model is better than another, and (b) whether a curve fit model is good in absolute terms.

The fit of a single exponential term fit to the concentration curve is referred to as an $E_1$ SET model and models that are sums of exponential terms as $E_2, E_3, E_4, \ldots, E_n$, respectively for $2, 3, 4, \ldots, n$ exponential terms. Current recommendations for assessing renal function or drug elimination after venous bolus injection are to use $E_{n>1}$ for fitting marker concentration curves with 8-13 blood samples. The physical model of linearly coupled, fast-mixing compartments inspired the use of SETs. SETs arise as one of three general solutions for the $n^{th}$ order linear homogeneous ordinary differential equation with constant coefficients.

The use of higher-order SET models leads to a host of problems. This is because when $E_{n\geq 2}$ SET models are used to model the concentration data they are often not robust enough to converge to statistically acceptable fits. Another problem is accuracy—it is well known that $E_1$ and $E_2$ SET models typically overestimate renal clearance. SET models fail to adequately fit the temporal dependence of marker concentration for radiochelated DTPA. In addition, SET models do not extrapolate properly, and they have small values for the areas under the temporal concentration curve (AUC), which is inappropriate for non-metabolized substances in the case of low (AUC large) to no renal function (AUC→∞).

A variation of the SET method of estimating CL uses numerical integration of area under the curve (AUC) of the concentrations of multiple samples over time and extrapolates the unmeasured area using mono-exponential fits to the last two hours of data. SETs and "AUC plus terminal mono-exponentials" are currently the only bolus models in use for estimating CL. This more complicated augmentation of normal SET models is used most commonly in the case of low renal function. Using mono-exponential extrapolations, it has been estimated that there is a 10% difference between the 4- and 24-hour AUC. It has been assumed that extrapolation using a "terminal" fit with a mono-exponential is less problematic the longer one waits to perform it. However, this observation also suggests that mono-exponential extrapolation consistently underestimates the extrapolated concentration. Another drawback of this method is the relatively long time period over which samples must be collected, causing the AUC method to border on the impractical.

Other curve fit models, gamma variates (GV), have been used to model the temporal dependence of the plasma concentrations of an assortment of drugs, for example, ampicillin, creatinine, chlorpheniramine, chlordiazeproxide, dexamethasone, terbutaline, oxyphenonium bromide, cefroxadin, idopyracet, cefroxadin, T3, pancuronium, inulin, and radiochelated DTPA. GV fits to late samples taken after one hour follow the temporal concentration data well in the fit region. However, direct fitting of a gamma variate function to the temporal concentration data is often ill-conditioned for CL, independent of which samples times are chosen for fitting.

In view of the aforementioned inadequacies of the prior art curve fitting methods, there remains a need to find a CL fit gold standard that agrees with current gold standards such as constant infusion.

SUMMARY OF THE INVENTION

According to the present invention, drug plasma concentration is measured in three or more, preferably four or more, blood samples taken over a period of time following bolus injection. The measured values are input into a computer processor programmed to execute a computer program comprising an algorithm that uses (a) the gamma variate (GV) function to model drug plasma concentration (the current trend is to use SET models) in the first place; (b) uses Tikhonov regularization to perform the fit; and (c) selects the regularization constant, λ (also commonly called the "shrinkage" factor), so that the error in the plasma clearance, CL, is minimized, producing one or more output values corresponding to renal function, including calculated (estimated) plasma clearance and error terms.

The resulting value(s) generated by the inventive method are stored in a computer memory and may be displayed on a human-readable display (monitor or printer) along with clinical data for the subject(s) from which specimens were obtained.

The inventive method is referred to as the Tk-GV method, where "Tk" stands for an implementation of Tikhonov regularization for optimizing fits to the dilutions curves, and "GV" for the use of the gamma variate as the functional form fit to these curves. The Tk-GV method uses regularization (i.e., smoothing) of the fit to the dilution curves that minimize the relative error in CL. This type of usage is called an adaptive fit. In this case, the adaptation is unusual in that CL and its errors are not estimated from the fit-data range of times, but from t=0 to ∞.

The Tk-GV algorithm is robust in that it readily converges to a global minimum. The inventive method is easier to use than the constant infusion, 24 hour AUC with mono-exponential extrapolation and the $E_2$ SET models. The results for CL are precise (2.7 to 3.7 ml/min SD), and agree with published corrections of CL from constant infusion of inulin and $^{51}$Cr-EDTA (ethylenediamine tetra-acetic acid), to within insignificant, 1 ml/min-1.73 $m^2$ or 0.6% errors, respectively. Thus, the Tk-GV model results reflect accurate renal function estimates without the need for correction factors, constant infusion, or increasing the time of data collection from 4 to 24 hours. Tk-GV provides CL and volume of distribution (V) information from as few as four samples over four hours, even when renal function is extremely low.

DETAILED DESCRIPTION

It should be noted that while the description refers to "drug plasma concentration", the inventive method is not limited to measurement of the CL for drugs and/or their metabolites alone, but is also appropriate for measurement of the CL for non-drug compounds, including the commonly-used solutions of inulin, creatinine and radiolabeled EDTA or DPTA for measuring glomerular filtration, as well as known and suspected toxins. It should also be noted that the measurement of excreted drugs and or CL may be achieved by a number of known methods including immunoassay, chemistry analyzers, mass spectrometer, gas or liquid chromatography, radioactive assay or images generated using computerized tomography or gamma camera.

Figure 1:
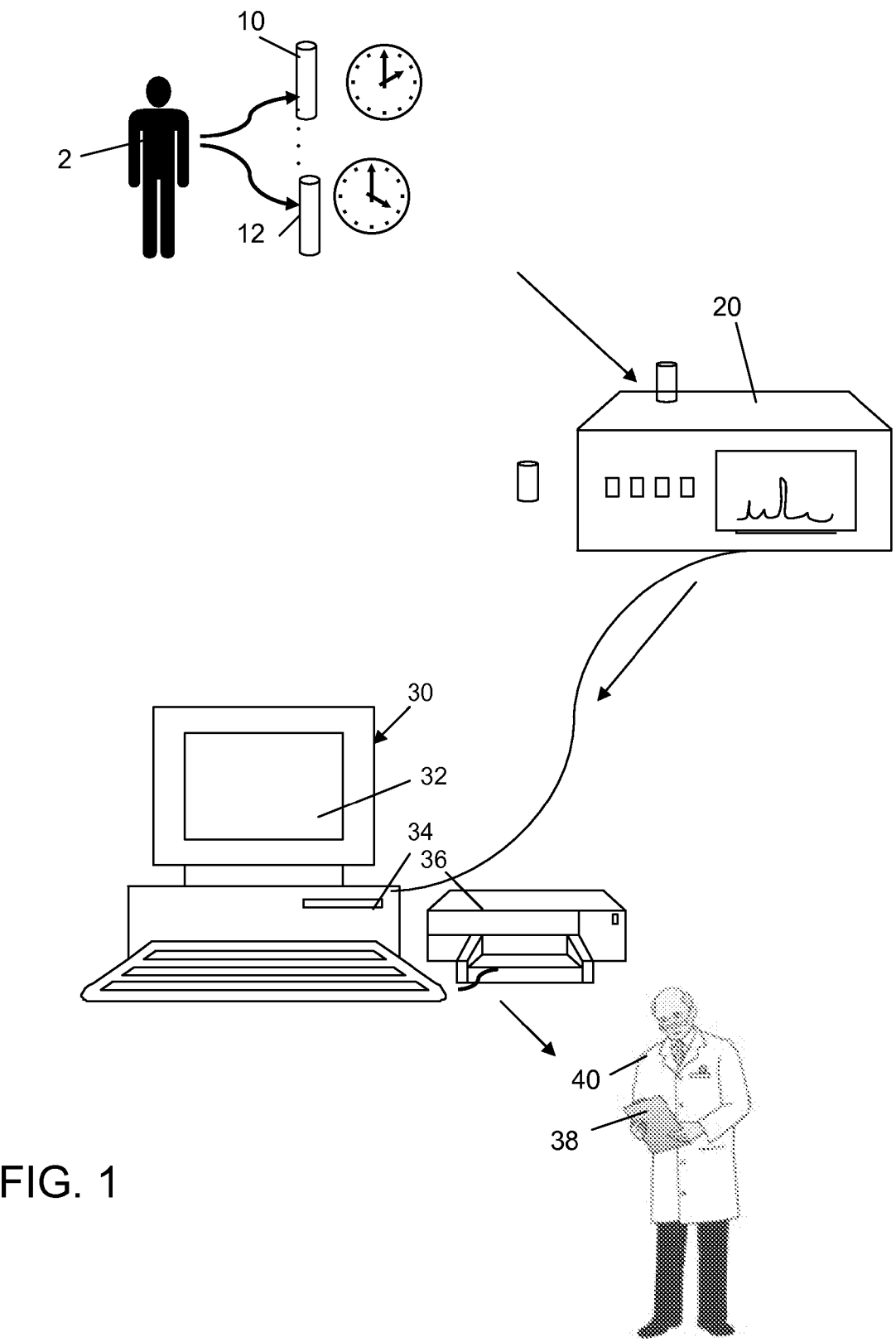
FIG. 1 is a diagrammatic view of an exemplary system for processing and reporting renal clearance results.

The inventive method is performed on a computer system, such as the arrangement shown in FIG. 1, comprising a processor 30, e.g., PC or APPLE® Mac®, with an appropriate operating system and programmed with software (a computer program product stored on a suitable computer-readable medium) to execute the algorithm and generate an output display for reporting to a researcher 40, physician or other health-care professional. The processor is also programmed to execute any necessary pre-processing as described in more detail below. A memory is included for receiving and storing the measured raw data as well as the processing results. Also in communication with the processor are an output device, including one or more of a graphic display monitor 32, a printer 36, and e-mail or web-based communications link for distributing the results of the algorithm executed on the input data to be accessed through one or more workstations, computers or mobile-handheld devices. In an exemplary embodiment, the algorithm is implemented using Mathematica™ version 7 computational and visualization software available from Wolfram Research, Inc. (Champaign, Ill.). Network-based processing is also contemplated, to allow researchers to download data from a remote location to a server that executes the inventive method and returns the analysis results on-line or via e-mail. Incorporation of additional hardware and/or software components to facilitate communication and processing functions as well as manipulation of the results, e.g., creating graphs and other visualization tools, will be readily apparent to those of skill and the art.

Still referring to FIG. 1, blood samples 10, 12 are taken from one or more subjects 2 at selected times following administration of the drug (or compound) of interest via bolus injection of known dosage. After sample preparation using procedures known in the art, plasma concentration of the drug is measured for each sample using conventional laboratory instrumentation 20 for such measurements (examples of such instrumentation are provided below) and the drug concentration values and time data are input into a processor programmed to execute the algorithm described in detail in the following discussion.

Figure 2:
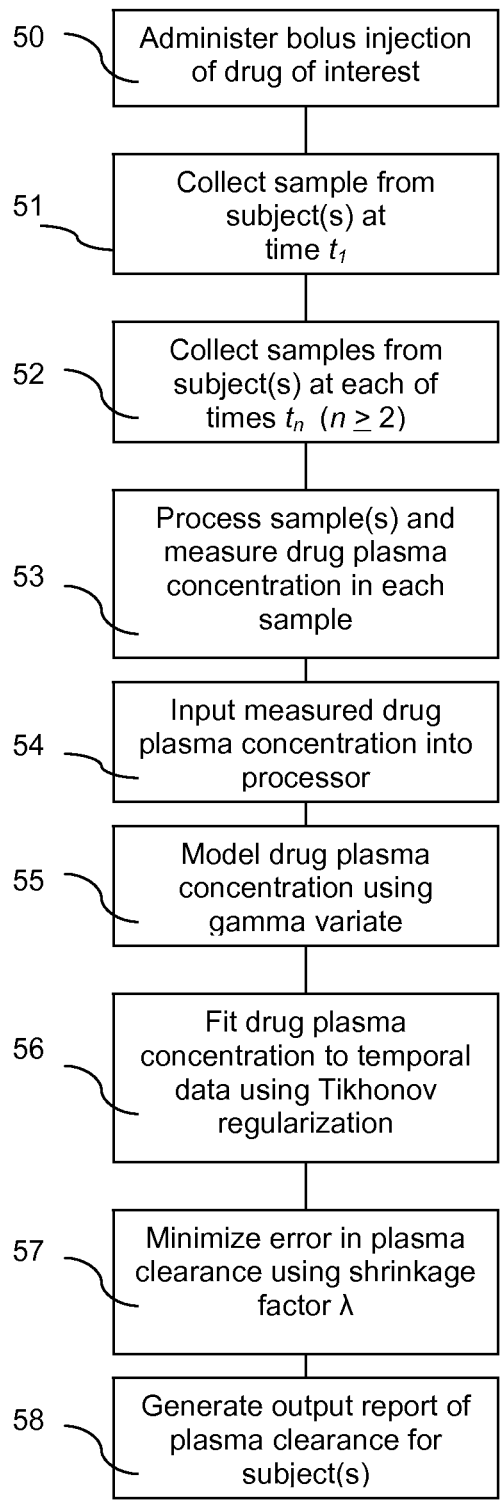
FIG. 2 is a flow diagram of the process flow for obtaining estimated renal clearance rate for a drug of interest.

FIG. 2 illustrates the steps of the inventive process, which are described in more detailed below. In step 50, the drug or other compound, e.g., inulin or radiolabeled DTPA, is administered by bolus injection. After a short delay at time $t_1$, e.g., 5 to 10 minutes after injection, a first sample is collected (step 51). Because there are a variety of different methods for measuring concentration, or clearance, of a label or tracer, the actual sample collection process and type of sample will also vary, and may involve collection of a blood sample, a urine sample, or even taking an contrast image using, e.g., X-ray tomography, MRI, PET, SPECT, ultrasound or other known imaging method. Selection of an appropriate sampling method, and a tracer to be used with the selected method, will be within the level of skill in the art. At least two additional samples are taken at times $t_2$ and $t_3$ (up to $t_n$) in step 52. Preferably, the samples will be taken at regular intervals, for example, every 5, 10 or 15 minutes, until the desired number of samples (n+1) are collected. In the preferred embodiment, n=3 or more, meaning that a total of 4 samples are sufficient to provide a good fit. These samples will preferably include one early sample, e.g., $t_1$=5 to 10 minutes after injection, and one late sample several hours, e.g., $t_{n+1}$1=4 hours, after injection.

After the samples have been collected they are processed in step 53 according to methods known in the art to quantify the amount of tracer or label in each sample. Such methods include immunoassay, liquid or gas chromatography, mass spectrometry, radioactive assay and contrast imaging. In step 54, the resulting data is input into and stored in a memory associated with a computer processor programmed to execute the Tk-GV algorithm. After pre-processing the data, e.g., normalization, in step 55, the processor executes an algorithm to model drug plasma concentration using a gamma variate curve fit. This provides an estimate of the terminal plasma concentration. Tikhonov regularization is performed in step 56 to fit the results produced using the GV method to the temporal data. As part of the regularization, although indicated as separate step 57, the error in CL (plasma clearance) is minimized by selecting a regularization or shrinkage factor $\lambda$. The resulting value(s) of CL is/are output by the processor to a graphical display or printer in step 58. Alternatively or in addition, the resulting values may be stored in the computer memory or on a computer-readable medium for further processing, e.g., to generate one or more plots of CL versus time for the patient who is being evaluated, or to provide the data as input to an overall evaluation of the patient using a combination of test results and other medical data and observations.

The Tk-GV method of the present invention achieves a precise and accurate fit through: (1) the use of Tikhonov regularization in performing the fit, and (2) selection of the regularization parameter, $\lambda$, so that the relative error in CL is minimized. The Tikhonov method thus appropriately discounts the fit to the early-time data when the plasma drug concentration is dominated by circulatory dilution and effects other than renal elimination or metabolism and dynamic equilibrium loss to the interstitium. The result is an accurate measurement of these effects without the need to wait many hours for quasi-static equilibrium to be fully established. This greatly reduces the required measurement time needed to achieve a given precision and accuracy. In addition, because the Tk-GV method by construction provides the most accurate value for CL for bolus injections, the Tk-GV can detect and measure levels of renal function much lower than the gold standard method of constant infusion, which for low levels of kidney function cannot be used as the infusate volume itself is not eliminated.

At the heart of the inventive Tk-GV technique is Tikhonov regularization. Tikhonov regularization is used in a variety of applications to remove solution ambiguity in ill-posed problems. The Tk-GV model implements regularization as an adaptive regularizing penalty function that rewards smoother fits to the data. Tk-GV is adaptive because the amount of smoothing is optimized using a controlling variable factor, $\lambda$, often called the shrinkage factor. Values for the shrinkage factor can be selected in a variety of ways. However, the goal is to measure CL, so the shrinkage factor will be adjusted to minimize the relative error of measuring CL, which error is expressed as the coefficient of variation (CV) of CL, i.e., $CV=s_{CL}/CL$, calculated from the propagation of small errors as described below.

In the first step of the inventive Tk-GV method, the GV function describes the observed (measured) terminal plasma marker concentration, $C_{obs}$, (in Bq per ml-min, or percent per min) where $$C_{obs} \rightarrow C(t) = Kt^{\alpha-1} e^{-\beta t}, \quad (1)$$

after some time that is dependent on CL (the limiting time is shorter for large CL). Note that GV is a function of only three parameters: $\alpha$, $\beta$ and K. After making the substitution $K \equiv \kappa \beta^{\alpha-1}$, Equation 1 becomes $C(t) \equiv \kappa(\beta t)^{\alpha-1} e^{-\beta t}$, where $\kappa$ has units of concentration, and $\beta t$ is dimensionless. Then for Equation 1 itself, K is a concentration scaling function, i.e., $K \equiv \kappa \beta^{\alpha-1}$. The $\alpha$ parameter is a dimensionless quantity related to the plasma leakage and scales the volume of distribution of Equation 3. In addition, $\alpha$ is the shape parameter for the gamma distribution. The $\beta$ parameter is the renal elimination rate constant, and is the reciprocal of the scale parameter for the gamma distribution. The formula for CL, the average rate of total clearance of plasma (in units of ml/min) for the GV model, in terms of the bolus dose, D, is $$CL = \frac{D\beta^\alpha}{K\Gamma(\alpha)} = \frac{D\beta}{\kappa\Gamma(\alpha)}, \quad (2)$$

where $\alpha$, $\beta$ and ln K are the parameters of the fit equation, $\Gamma(\alpha)$ is the gamma function evaluated at a value of $\alpha$. The volume of distribution (ml), V, can be obtained from Equation 1 through use of the Mean Residence Time (MRT) integration, which gives $$V = MRT \cdot CL = \frac{\alpha}{\beta} CL. \quad (3)$$

If $C_{obs}$ (t) follows a GV law, then the concentration obeys $$\frac{dC}{dt} = \left[\frac{\alpha-1}{t} - \beta\right] C, \quad (4)$$

where $\beta = \beta' \chi$, $\chi$ is the rate of removal by metabolism and $\beta$ is the renal removal rate, which follows from differentiating the GV function with respect to time. The first term, $(\alpha-1)C/t$ represents loss of marker presumed here to be to the interstitium. The second term, $-\beta C$, is the first order kinetic term, herein renal loss only as the markers are inert. When the AUC method is used for determining CL with a GV for the concentration, both clearances are included. Since the first term is time dependent, CL is also time dependent, and CL as calculated from the dosage AUC, is a concentration-averaged plasma-clearance attributable to CL:

$$D = \langle CL_{total} \rangle \int_0^\infty C_{obs}(t) dt, \text{ or, } \langle CL_{total} \rangle = \frac{D}{\int_0^\infty C_{obs}(t) dt}, \quad (5)$$

where $\langle CL_{total} \rangle$ is concentration weighted for the entire time interval from zero to infinity, and where the term $$\int_0^\infty C_{obs}(t) dt$$

is referred to as the Physical Area Under the Curve, Phy-AUC (in percent dosage-min, mg-min, or Bq-min). Note that CL of Equation 2 is the total plasma-clearance and is greater than renal clearance of plasma: $CL_{urine}$ from urinary collection, which latter is a function of $\beta$ alone.

Tk-GV fitting, unlike OLS fitting, does not always provide an interpolation of the concentration data that has the smallest residuals. The Tk-GV fit is biased. For an over-determined system of linear equations, Ax=b, the Tikhonov regularization (Tk) of this problem introduces the penalty function Γx and seeks to find a solution that minimizes $\|Ax-b\|^2+\|\Gamma x\|^2$, which is the square of a norm of the residuals, $\|Ax-b\|^2$, plus the square of a norm of the product of the Tikhonov matrix, Γ, with the x fit parameters (unknowns). The more general $\Gamma^T\Gamma$ regularizing term is often, as it is here, replaced by λI, where I is the identity matrix, and λ is a Lagrange (i.e., constraint) multiplier, also referred to as the shrinkage, Tikhonov or damping factor. It should be noted that although it offers no computational advantage to do so, ridge regression, used here, is Tikhonov regularization with correlation scaling that standardizes λ values. Further, λ=0 is equivalent to the problem of minimizing the norm $\|Ax-b\|^2$, which is most commonly solved using ordinary least squares (OLS).

In effect, for decreasing renal function, increased regularization (i.e., higher value of the shrinkage factor) is applied as the relative importance of un-modeled effects extend later and later into the sample measurement times. The Tk-GV method's selection of the value of the shrinkage term needed to minimize the error in CL provides an effective means of measuring small values of CL that were unphysical, complex number solutions, by OLS GV fitting. This same constraint allows the Tk-GV method to provide realistic values of the volume of distribution for vanishingly small CL values when other techniques (even constant infusion) cannot measure V. However, as the shrinkage factor increases, the data becomes increasingly unimportant and eventually is not included in the fit. Thus, results with CL very close to zero (such that λ≫1) are suspect and it is prudent to examine all aspects of the procedure.

A common constraint for regression is to require the fit function to pass through the data mean point (a.k.a., the centroid, $\bar{x},\bar{y}$). Because the logarithm of concentration is the more homoscedastic quantity, it is common to fit the logarithms of marker concentration rather than the concentration itself. Thus for the Tk-GV method, Equation (1) becomes ln C=lnK+(α−1)ln t−βt, where the constant term ln K need not be independent, but can be determined from the other fit parameters using a mean value constraint. Taking averages over the data $$\ln K = \overline{\ln C(t)} - (\alpha-1)\overline{\ln t} + \beta \bar{t} = \bar{b} - (\alpha-1)\bar{a}_1 + \beta\bar{a}_2, \quad (6)$$

such that $\bar{b}$, $\bar{a}_1$ and $\bar{a}_2$ are data constants, where $\bar{b}$ is the mean value of the logarithms of the concentrations, $\bar{a}_1$ is the mean of the logarithms of the sample times and $\bar{a}_2$, is the mean of the sample times.

As shown by Equations 7-12, Equation 6 can be used to remove K from the formula for CL given in Equation 2, and an expression can be derived for the errors in CL with only α and β as independent parameters, and where $\bar{b}$, $\bar{a}_1$ and $\bar{a}_2$ are constants.

In general, the formula for the propagation of errors in the quantity x of independent parameters u, v, . . . , x=f(u, v . . . ), is given by $$s_x^2 = s_u^2\left(\frac{\partial x}{\partial u}\right)^2 + s_v^2\left(\frac{\partial x}{\partial v}\right)^2 + 2s_{uv}\left(\frac{\partial x}{\partial u}\right)\left(\frac{\partial x}{\partial v}\right) + \ldots, \quad (7)$$

which is the sum of variances and covariances scaled by their respective derivatives. Where the variances and covariances are calculated as usual, which are available during the process of the Tikhonov regularization as $$s_x^2 \equiv \frac{1}{N-1}\sum_{i=1}^{N}(x_i-\bar{x})^2, \quad s_u^2 \equiv \frac{1}{N-1}\sum_{i=1}^{N}(u_i-\bar{u})^2, \quad (8)$$

$$s_v^2 \equiv \frac{1}{N-1}\sum_{i=1}^{N}(v_i-\bar{v})^2, \quad s_{uv}^2 \equiv \frac{1}{N-1}\sum_{i=1}^{N}(u_i-\bar{u})(v_i-\bar{v})$$

where $\bar{x}$, $\bar{u}$ and $\bar{v}$ are the mean values. For Equation 2: CL=Dβ^α/[KΓ(α)], D is the dose and α, β and ln K are the parameters of the fit equation ln C=ln K+(α−1)ln t−βt. However, for Tikhonov regularization, recalling Equation 6, $$\ln K = \bar{b}-(\alpha-1)\bar{a}_1+\beta\bar{a}_2, \quad (9)$$

where $\bar{b}$ is the mean value of the logarithm of m concentrations: $\bar{b}=\Sigma \ln C_i/m$, $\bar{a}_1$ is the mean logarithm of m sample times: $\bar{a}_1=\Sigma \ln t_i/m$; and where $\bar{a}_2$ is the mean sample time: $\bar{a}_2=\Sigma t_i/m$. To apply Equation 7 to Equation 2, one may first substitute K of Equation 9 into Equation 2

$$CL = \frac{D\beta^\alpha}{e^{\bar{b}-(\alpha-1)\bar{a}_1+\beta\bar{a}_2}\Gamma(\alpha)}, \quad (10)$$

and take the total partial derivatives of the resulting equation with respect to α and β yielding $$s_{CL}^2 = CL^2\left[s_\alpha^2(\bar{a}_1+\ln\beta-\Psi(\alpha))^2 + \right. \quad (11)$$
$$\left. s_\beta^2\left(\frac{\alpha}{\beta}-\bar{a}_2\right)^2 + 2s_{\alpha\beta}(\bar{a}_1+\ln\beta-\Psi(\alpha))\left(\frac{\alpha}{\beta}-\bar{a}_2\right)\right],$$

where capital psi of alpha: $\Psi(\alpha)$ is the digamma function of α and $\Psi(\alpha)=d[\ln\Gamma(\alpha)]/d\alpha=\Gamma'(\alpha)/\Gamma(\alpha)$. Also, note the term $CL^2$, has been factored out from the total derivative of the right hand side of Equation 2. To obtain a quantity of interest for minimizing, Equation 11 is rewritten as the square of the relative standard deviation of CL, which gives the error in CL:

$$\left(\frac{s_{CL}}{CL}\right)^2 = s_\alpha^2(\bar{a}_1+\ln\beta-\Psi(\alpha))^2 + \quad (12)$$
$$s_\beta^2\left(\frac{\alpha}{\beta}-\bar{a}_2\right)^2 + 2s_{\alpha\beta}(\bar{a}_1+\ln\beta-\Psi(\alpha))\left(\frac{\alpha}{\beta}-\bar{a}_2\right),$$

where $(s_{CL}/CL)^2$ is the squared relative standard deviation, a.k.a., squared coefficient of variation $(CV)^2$ of CL. Minimizing the right hand side of Equation 12 as a function of the shrinkage, λ, selects a λ value that produces the CL value with the smallest relative error achievable. Also, minimizing the relative error in CL is indispensable for making reliable measures of CL when CL is small.

The variance of V is similarly calculated by taking the total partial derivative with respect to α and β of the substitution of Equation 12 into Equation 2 substituted into Equation 3 yielding $$s_v^2 = V^2\left[s_\alpha^2\left(\frac{1}{\alpha}+\bar{a}_1+\ln\beta-\Psi(\alpha)\right)^2 + s_\beta^2\left(\frac{\alpha}{\beta}-\frac{1}{\beta}-\bar{a}_2\right)^2 + \right. \quad (13)$$
$$\left. 2s_{\alpha\beta}\left(\frac{1}{\alpha}+\bar{a}_1+\ln\beta-\Psi(\alpha)\right)\left(\frac{\alpha}{\beta}-\frac{1}{\beta}-\bar{a}_2\right)\right].$$

The square root of the variances of CL of Equation 11, and of V of Equation 13 are the standard deviations, SDs, (i.e., $s_{CL}$ and $s_V$) of the errors of measurement of individual CL and V values.

While Equation 12 and the corresponding equation for $s_V$, Equation 13, allow calculation of the standard deviations of CL and V, another method of independently calculating these errors uses the jackknife method and is used in Example 1 below to verify the range of small errors in CL and V.

EXAMPLES

Data used for testing of the performance of the Tk-GV method were 41 $^{169}$Yb-DTPA (diethylenetriamine penta-acetic acid) studies with eight samples taken at approximately 10, 20, 30, 45, 60, 120, 180, and 240 min after injection, and five additional $^{99m}$Tc-DTPA studies with nine samples taken at 5, 10, 15, 20, 60, 70, 80, 90 and 180 min after injection.

Tikhonov regularization (Tk) is widely used in ridge regression in statistics, and is a standard feature of many statistical packages including SPSS® (from SPSS, Inc., Chicago, Ill.), R (R Project) and MATLAB® (Mathworks, Inc., Natick, Mass.). As used in the exemplary implementation, MATHEMATICA® version 7 (Wolfram Research, Champaign, Ill.) has a run time of several seconds for convergence to 16 decimal places. The algorithm was checked against SPSS® version 15. Global-optimization-search numerical techniques can enforce convergence. While these methods should find the global minimum (of Equation 12), practical implementation may only find a local minimum. To gain confidence that the results are global minima, regressions with multiple random starting conditions were obtained for each sample combination. This process was carried out for several different regression methods. In difficult cases, i.e., noisy cases from leaving out four samples (L4O), 70,000 regressions were performed with each method. Using L4O, there were 3500 selections of different subsets of the data and each was regressed 20 times to find the best regressions using each of three methods: Nelder-Mead, simulated annealing, and differential evolution. In no single case out of 3500 were the results of any of the three fits methods for a given set of samples different from the fits results of the other two methods to 16 decimal places. To obtain converged solutions to agree within 16 decimal places required a computational precision of more than 32 decimal places, and techniques internally accurate to 40 decimal places were used.

Four examples are used to illustrate different tests of the suitability of the Tk-GV model: Example 1 uses characterization of parameters from Tk-GV fits using analysis of variance (ANOVA) to examine statistical validity of the model; Example 2 uses effects of sample-subset selection on Tk-GV model parameters to examine conditioning (stability) of the model, e.g., when different temporal ranges of samples are used; Example 3 uses characterization of Tk-GV residuals (i.e., differences between the model and the data) to examine unmodeled dilution; and Example 4 uses error testing of extrapolation and includes the section on comparison with published "gold standards."

The results of the four examples are compared to those of conventional curve fitting models, i.e., the sums of exponential terms models $E_1$ and $E_2$ and OLS GV fits without regularization. In performing these tests, fits to various subsets of the concentration samples collected for each patient are examined. The fits with results least affected by noise are those that use all m samples, where m is 8 or 9, the results of which are presented in Examples 1, 2 and 4. By performing multiple fits to various subsets of the samples for each patient, a variety of insights into the sensitivity of the results to sampling times and an independent analysis of error of parameter values can be gained. To achieve these goals, the sample-subset selection schemes are of three types. (i) The first method is leaving out a specific number of samples, e.g., LOO (leave one out). This is done in Examples 1 and 3. (ii) The second method is to leave out temporally sequential samples, i.e., the earliest and latest samples. This addresses the question of whether it matters when the samples are collected. This is a severe test of how a model performs when forced to fit temporally restricted data. This is done in Example 2. Example 4 (Extrapolative error) leaves off the last sample and compares this to all sample values of concentration and of CL and V. However, this is not exhaustive in the sense that it does not include all of the combinations for leaving out data. (iii) The more exhaustive test of leaving out all possible sample combinations was performed especially to test the theoretical limits of Tk-GV parameters in Example 2 and to develop the numerical techniques that robustly converge to the global minima of the relative error of CL in high-noise conditions with sparse data.

Example 1

Characterization of Parameters from Tk-GV Fits

Tk fit parameter calculations include tolerances as part of the Tk regression process. However, since Tk-GV attempts to minimize $s_{CL}$/CL, i.e., a tolerance, it is prudent to crosscheck the intrinsic Tk-GV tolerance results. Note that bootstrap regression, which randomizes residuals in time, is not compatible with time-based adaptive fitting. Instead, the Tk-GV parameter tolerances were crosschecked with LOO (Leave One Out, jackknife) analysis of variance for CL and V (373 trials total or 8 trails for each of 41, 8-sample patients and 9 trials for each of 5, 9-sample patients). The resulting jackknife variances are corrected for leaving data out under highly correlated resampling conditions. It is also possible to use L2O (leave two out), L3O (leave three out), and so forth. In general, leaving d items out (LdO) produces a $d^{th}$ variance estimator. To calculate the standard deviation (SD) of a parameter of interest, one merely needs to take the square root of the variance for that parameter, which is given by $$s_x^2(m) = \frac{m-d}{d} \sum_{i=1}^{N} \frac{(x(LdO_i) - \bar{x}(LdO))^2}{N}, \quad (14)$$

$$N = \binom{m}{m-d} = \frac{m!}{d!(m-d)!},$$

where $s_x^2(m)$ is the variance of variable x calculated from the m LdO trials, $$\binom{m}{m-d}$$

is the number of combinations of the LdO trials of m samples taken m−d at a time. For example, to find the 8-sample variance of V using LOO, Equation 14 becomes $$s_V^2(8) = (7/8) \sum_{i=1}^{8} [V_i(LOO) - \bar{V}(LOO)]^2,$$

where $\bar{V}(LOO)$ is the mean LOO V result. Equation 14 is used only once as LOO, in Table 1, below. However, leaving out data has other important uses, e.g., for testing algorithms, and extremes of parameter ranges.

TABLE 1

Summary of Tk-GV results showing no out-of-bounds, i.e., nonphysical, parameter values[a]

| | Parameters from Tk-GV fits | | | | | | | | Jackknife LOO | |
|---|---|---|---|---|---|---|---|---|---|---|
| Percentile | $\lambda$ | ln K | a | $\beta$ min$^{-1}$ | CL ml/min | V ml | $s_{CL}$ ml/min | $s_V$ ml | $s_{CL}$ ml/min | $s_V$ ml |
| 0th | 0 | −5.364 | 0.5945 | 0.000106 | 1.242 | 7404 | 0.1876 | 63.02 | 0.1075 | 18.71 |
| 25th | 0.01216 | −4.537 | 0.7140 | 0.002169 | 44.39 | 13127 | 1.404 | 288.0 | 0.8542 | 200.6 |
| 50th | 0.09308 | −4.280 | 0.7749 | 0.003452 | 74.28 | 16275 | 2.510 | 474.5 | 1.696 | 384.8 |
| 75th | 0.2610 | −3.991 | 0.8649 | 0.004556 | 105.5 | 18490 | 3.703 | 690.6 | 2.708 | 531.9 |
| 100th | 2.197 | −3.386 | 0.9895 | 0.009080 | 157.6 | 31124 | 6.222 | 1344 | 10.51 | 1283 |
| Probability | <0.0001 | 0.970 | 0.158 | 0.123 | 0.162 | 0.166 | 0.116 | 0.113 | <0.0001 | 0.004 |

Table 1 comments:
[a]Parameter values do not correspond horizontally, for example, the 0$^{th}$ percentile CL value is not the 0$^{th}$ percentile V or $s_G$ value. The 46 patient studies parameters are presented in percentile from smallest to largest from fitting all of the samples for each patient (8 and occasionally 9 samples). Parameters for the fit equation C(t) = K t$^{\alpha-1}$e$^{-\beta t}$ were regressed by Tikhonov regularization with shrinkage factor, $\lambda$. The resulting plasma-clearance rates, CL, and volumes, V, are listed. The shrinkage factor, $\lambda$ (dimensionless) is the Tikhonov "smoothing" parameter. $\alpha$ is also dimensionless. The standard deviations, $s_{CL}$ and $s_V$ are calculated by two independent methods. The first is directly from Tikhonov regularization of m samples, using the standard formula for propagation of small errors.
[b]The second method uses jackknife of 373 leave one out (LOO) Tk-GV trials (m − 1 samples).
[c]The Shapiro-Wilk probability is one method of testing for a normal distribution (ND). Note that ln K is a ND.

Results: The test performed in Example 1 examines the physicality of Tk-GV parameters. The most important observation from Table 1 is that the Tk-GV parameter values have physically sensible ranges and tight tolerances. For example, the GV equation's $\alpha$ parameter varied only from 0.59 to 0.99, and no negative (or vanishingly small) β-values occurred. This represents an improvement over the OLS GV fits, which had 5/46 problematic β-values. However, Table 1 does not permit a horizontal comparison between parameters, so one must examine how the parameters covary. In the general context of Tk regularization, $\lambda$ has no physical meaning. However, because 2 is used to minimize error for Equation 12, $\lambda$ becomes a measure of how much smoothing/departure from OLS fitting is needed to extract CL-values. For $\lambda$=0, the Tk-GV fit to the data is equivalent to an OLS fit of a GV function to the data. The median value of shrinkage was relatively low (0.09, Table 1). From the individual parameter results themselves, the shrinkage factor $\lambda$ took on values that varied from zero (2/46 times) to greater than one (3/46 times). The two 0$^{th}$ percentile, $\lambda$=0, values occurred at CL values of 147.5 and 121.7 ml/min, values easily in the highest quartile of CL values. This suggests that the GV function fits better for high CL values. On the other hand, there were three outcomes with high shrinkages, $\lambda$>1. These high shrinkage values correspond to the lower values of CL and β, but quite average values of V and high values of $\alpha$ (0.95<$\alpha$<0.99). The values CL and β covary, and, $\alpha$ closest to 1 and the values of β closest to zero are correlated. This limiting behaviour is strong, and otherwise, $\alpha$ and β are not especially related. For CL,β→0 and the Tk-GV model, $\alpha$→1 quickly, and V→CL/β becomes a constant ratio. To see how this arises, as $\Gamma$(1)=1, by using the form of Equation 2 employing $\kappa$, one obtains that for low function ($\alpha$≈1) CL/β≈D/$\kappa$≈V. Since concentration is relatively static for low function, and since $\kappa$, the concentration constant, is even tamer, both V and vanishingly small CL should be accurately and simultaneously measurable. This limiting behavior is a result of minimizing the relative error in CL given by Equation 12, which then effectively acts as an additional constraint equation.

Thus, for Tk-GV, if $$\lim_{\alpha \to 1} \beta \to 0,$$

one should be able to use the Tk-GV method to measure CL and V for patients with very low renal function as then CL/β≈D/$\kappa$≈V. When the value of CL becomes small, unmodeled dilution increasingly predominates, and it takes more and more regularization to produce the CL estimate (see Example 3 for more detail). Moreover, the smallest errors occur when the quantity of interest, CL, is the largest. Large CL values are easier to measure precisely and $\lambda$ are then small or zero with little regularization needed to get a good fit. To test these findings under more strenuous conditions, data can be left out, as described below.

Example 2

Effects of Sample-Subset Selection on Tk-GV Model Parameters

In this example, the Tk-GV models are fit to subsets of each patient's data. There are many ways to select subsets of samples for studies containing 8 or 9 samples. Restricting the sample subsets of the 8-sample dataset that have temporally consecutive samples that drop as many as 4 early or late samples has an advantage. While this selection is not exhaustive, it allows for plotting of the effect of the widest available spread of mean sample times on the values of the fit parameters $\alpha$ and β. These parameters, $\alpha$ and β are the only independent parameters, as per Equation 6, of the Tk-GV model. The behavior of this model with respect to the extremes of mean sample times can be plotted as the frequency of out of bounds values of $\alpha$ and β for increasing mean sample time. The obvious targets for analysis are the desired measures for performing the testing: CL and V. But, also of interest is the number of cases for which Tk-GV fits predict vanishingly small renal function values compared to the frequency of similar results from ordinary GV regression fits to the data. This is examined by leaving out four or fewer samples of the 8 or 9 available for each dilution study.

Figure 3:
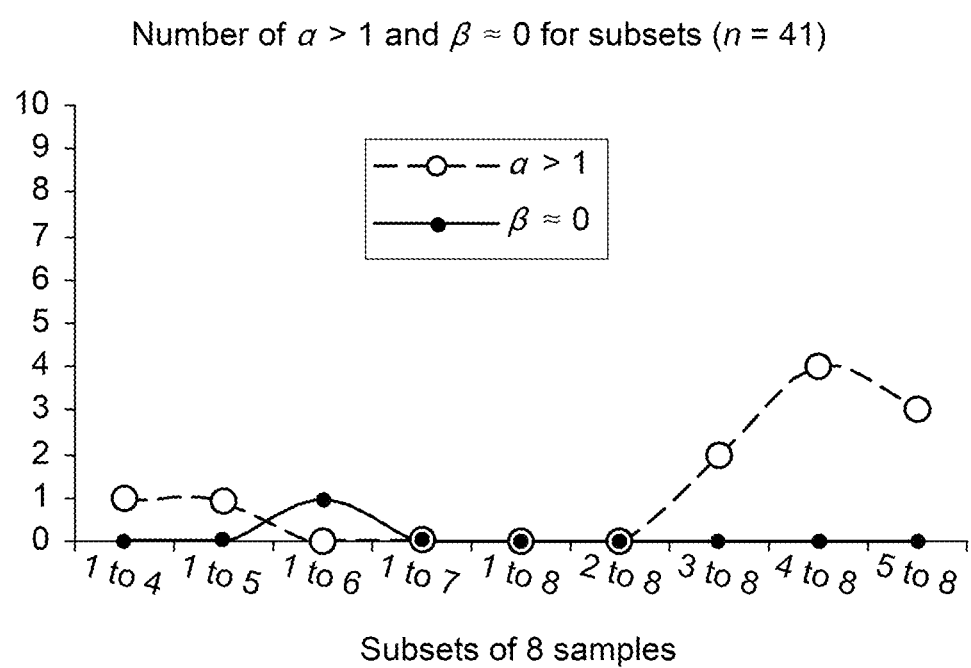
FIG. 3 is a plot of the frequency of occurrence of problematic values for the parameters α and β for Tk-GV fits for various subsets of samples.

Results: FIG. 3 presents the frequency of occurrence of problematic values for the parameters $\alpha$ and β from Tk-GV fits to various subsets of samples taken from the 41 cases from the 8 sample dataset. From left to right, this plot presents earliest to latest sample subsets. The plot provides a quick visualization of when problems with fitting arise. In FIG. 3, the three earliest and the three latest sample subsets contain problematic $\alpha$>1 solutions and in one instance, a β≈0 solution. If an $\alpha$≤1 constraint were used this would produce an E$_1$, single exponential term (i.e., low quality, inflated CL estimating) fit to result. Consequently, the best strategy is to include enough sampling time between the first and last samples to avoid an appreciable likelihood of producing an α>1 or when inappropriate, β≈0 result.

In FIG. 3, the open circles and dashed lines show the frequency of α from Tk-GV fits being out of bounds (α>1) for all samples or subsets of all samples for the 41 cases from the 8 sample dataset. Problems with detection of CL are shown with solid circles and solid lines, i.e., for β close to zero ($\beta<1\cdot10^{-7}$, CL<0.001). There were no very small values of CL using Tk-GV for the 5 patients from the 9 sample dataset. Note that there are no questionable results for α or β when only one sample, or no samples, is left out (i.e., samples sets 1 to 7, 1 to 8, and 2 to 8).

FIG. 3 suggests a major improvement in conditioning of the Tk-GV versus the OLS GV models. It is clear that β≈0 occurrences are significantly less frequent for Tk-GV (1/369) than for OLS constrained GV fitting (62/369). For the Tk-GV versus OLS GV fitting, the frequency of α>1 (11/369 versus 26/369) is also less for leaving out samples by this method.

The trend noted in Example 1 above was that as α→1, β→0. To investigate this trend further, other sample subsets were explored to search for systematic problems for which $$\lim_{\alpha \to 1} \beta \to 0$$

is not true. For the leave out 4 or fewer samples, there are 7963 different subsets of the data, having a total of 99 fits that produce a value of α>1 (1.24% of all of the trials). Of the 7963 data subsets, 3089 omit the first 5 or 10 min sample, and 93 of these had values of α that were greater than 1 (3.01% of the 3089 trials). For the 4874 trials that included the first sample, there were only 6 with α>1 (0.12% of the 4874 trials). In practice, it appears that both early and late-time samples are needed to provide good conditioning to the fit in the sense of avoiding α>1 or β≈0 solutions. It is the β≈0 solutions that best illustrate $$\lim_{\alpha \to 1} \beta \to 0.$$

The values for β and CL are trivially small only 9 times (0.11%) amongst the 7963 combinations for leaving out 4 or fewer samples. All 9 of these only occur for patient 20 when at least the $7^{th}$ and $8^{th}$ samples (i.e., the last two) are left out. Using all samples, patient 20 has the smallest CL (1.24 ml/min) of all of the 46 patients, and a V of 11631 ml, found with a relatively high smoothing value of λ=1.61 and high α=0.9895. The median CL for patient 20 with L4O (i.e., from 4 samples) is 1.69 ml/min, or only slightly different from the all-8 sample data set result of 1.24 ml/min. However, of the 70 L4O trials for patient 20, there are 5 sample combinations (7.14%) with nearly zero renal function. These examples show how remarkably stable the determination of V is for the Tk-GV method. For patient 20, if one leaves out samples 1, 4, 7, and 8, the resulting Tk-GV parameters become α=1 (exactly to 40 decimal places), $\lambda=7.34\cdot10^{41}$ (very high smoothing), $CL=1.71\cdot10^{-43}$ ml/min, $\beta=1.53\cdot10^{-47}$ min$^{-1}$, and V=11164 ml. This strongly demonstrates that the ratio of CL to β, i.e., V, is preserved by the Tk-GV method even when renal function is trivially small. From patient 20, L2O (i.e., samples 8, 7), V=11113 ml, and α=0.999999999823346. An upper limit of α=1 was not found in prior works which performed OLS GV fits. However, α≤1 is consistent with $CL_{total}(t)>CL_{urine}(t)$, i.e., total plasma clearance is greater than renal clearance from urinary collection. When α≈1 yielding vanishingly small CL-values, the Tk-GV method found a GV fit with a constant concentration, c(t)≈K. So leaving out data can make the data noisier, and cause a problem in detecting already small CL. In that case, the residuals, $C_{obs}(t)-C(t)$, become $C_{obs}(t)-K$. In other words, for vanishingly small renal function, the residuals become a function of time and generally decrease in time. This implication is confirmed in the results of Example 3 below.

Figure 7:
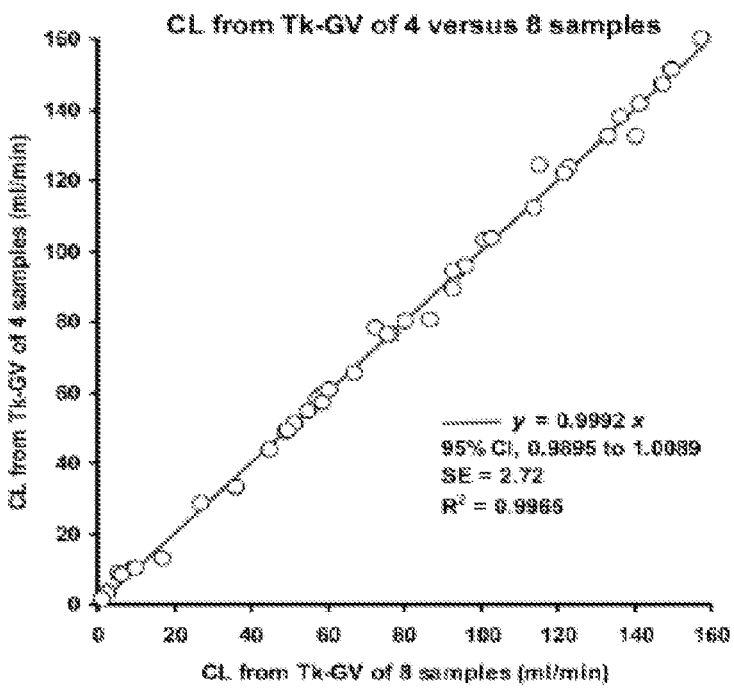
FIG. 7 is a plot of the regression of 8 samples versus 4 samples for the TK-GV CLs.

Based on the above results, it was determined that as long as both early and late times are included, only 4 samples are needed to obtain a Tk-GV solution. (This can be contrasted with the minimum number needed for an $E_2$ SET model, even from simulated, i.e., "perfect" $E_2$ SET data, which would be 6 samples.) A comparison of the results indicated that there was not a great deal of difference between using 4 and 8 samples, which is clearly seen from FIG. 7. For example, if one chooses the 10, 30, 120, and 240 min samples and compares this to using all samples (Passing-Bablok method), the intercept is insignificantly different from zero, i.e., −0.1554 ml/min (95% CI−1.146 to 0.6274 ml/min), the slope is insignificantly different from 1, i.e., 1.001 (95% CI 0.9897 to 1.016), and the OLS $R^2$ value is 0.9965 with a standard error of 2.75 ml/min. One can also set the x-y intercept to 0,0 and plot this as a maximum likelihood regression as in FIG. 7.

Example 3

Characterization of Tk-GV Residuals

The test performed in this example considers the structure or temporal trend of the residuals (the differences between the data and the Tk-GV fits) for various Tk smoothings, λ, and renal rate constants, β. In general, one would only expect the mean residuals from ordinary least squares (OLS) regression to be zero for a perfect match between a model and the data. However, to find a more precise estimate of CL, Tk-GV fitting introduces bias to the otherwise unbiased OLS solution. In other words, for the Tk-GV method, biased residuals from fitting early times are desired given that the terminal GV behaviour sought is inappropriate to earlier times. Thus, inspection of these residuals is revealing, and the residuals are examined in some detail in this example.

Figure 4:
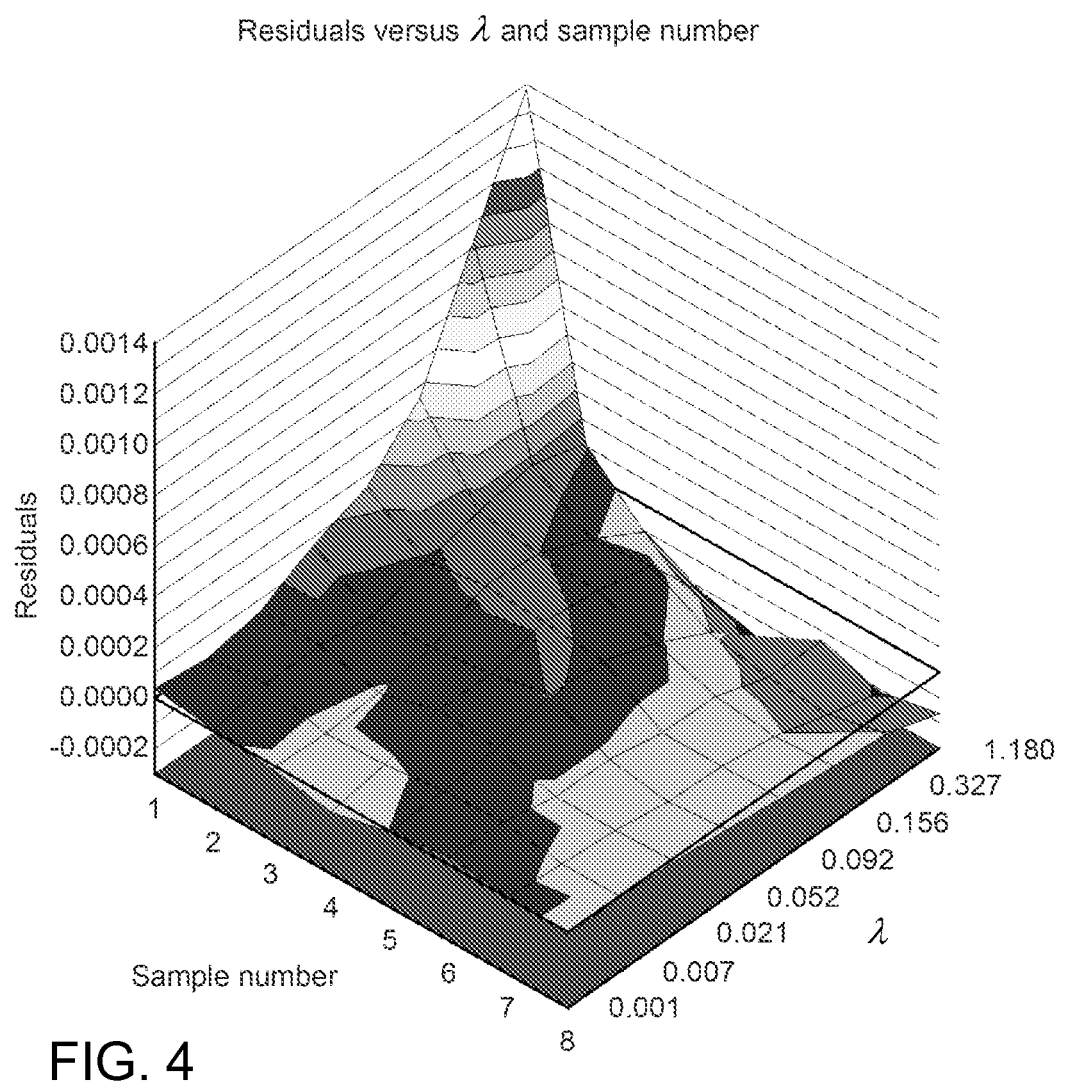
FIG. 4 is a three-dimensional plot of mean residuals versus shrinkage 2 for sample numbers 1 through 8.
Figure 5:
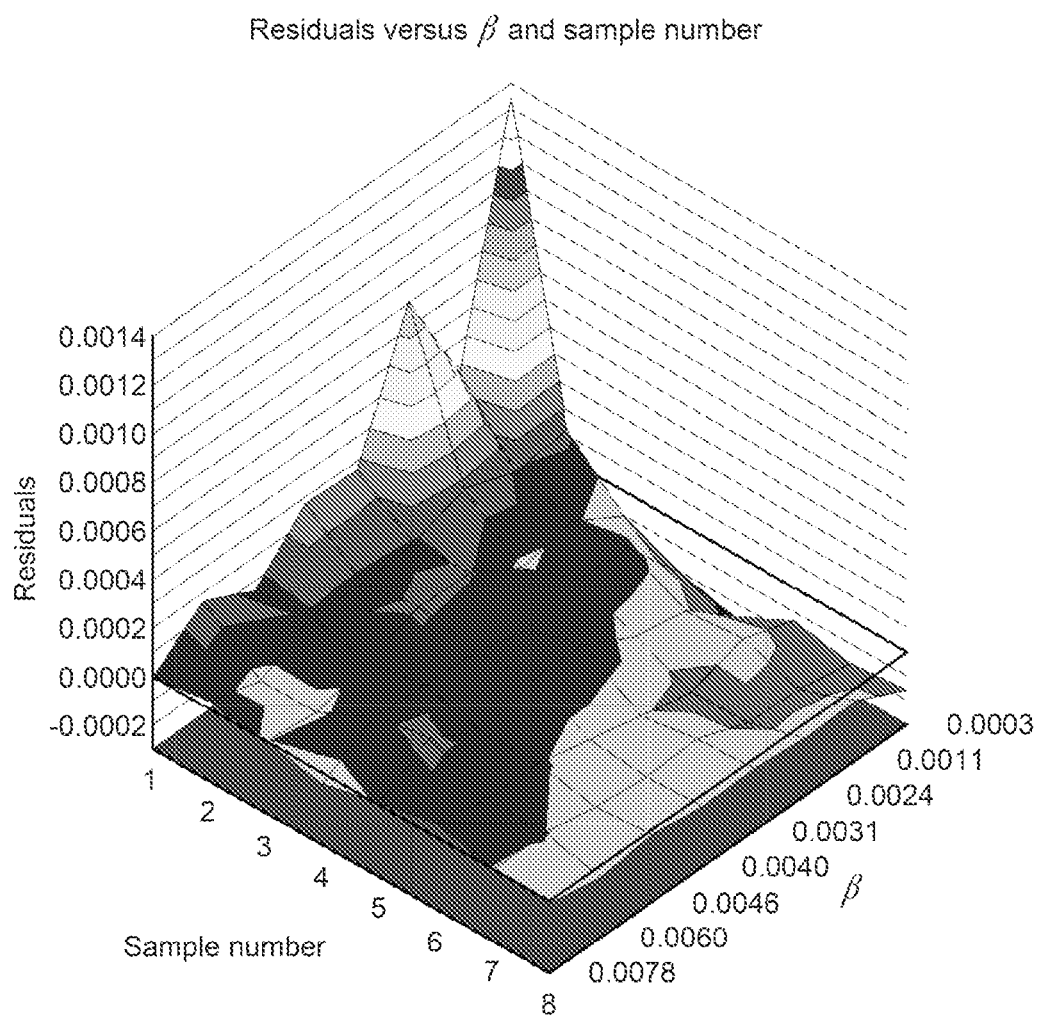
FIG. 5 is a three-dimensional plot of mean residuals versus renal rate constant β for samples 1 through 8

Results: FIG. 4 shows the mean residuals from Tk-GV regressions of the 41 eight sample cases. These residuals are plotted for LOO fits in 8 equal octiles of increasing shrinkage values having 41 regressions in each octile for 328 regressions. When λ=0, the Tk-GV solution is unbiased and identical to the OLS solution. As can be seen in FIG. 4, when the shrinkage, λ, is very small, the residual function, or difference between the fit and the concentrations, is also small (mean first octile λ=0.001, and more generally for all 46 LOO series, λ=0, 17/373 times (4.6%) in 11/46 patients). This is consistent with the smallest relative errors for measuring CL corresponding to the smallest λ, and the largest CL values. That is, for high normal renal function, the GV model often fits the data without the need for Tk smoothing. FIG. 5 confirms that for high renal elimination rates, β, the residuals are small. As the λ values increase in FIG. 4, and the β values decrease in FIG. 5, the residuals especially for the first sample(s) increase so that the fit underestimates the concentration for early samples. Moreover, for large λ or low β values, the fit overestimates the concentrations of the late samples. In summary, as the shrinkage increases, so does the regression bias needed to find the Tk-GV fit with the minimum error in CL. FIG. 5 shows graphically how large the bias becomes when estimating very low renal function. In effect, when there is zero renal function, the Tk-GV fit is a flat-line, and the residual concentration reflects unmodeled dilution, with high initial concentration, that decreases with time. On the other hand, when $\lambda=0$ and there is high renal function, the Tk-GV fit solutions becomes OLS GV regressions and fit the concentration curves well.

Example 4

Extrapolative error

Extrapolative error, $\epsilon_{extrap}$, is defined as the differences between the m and m−1 sample fit functions evaluated at the time of the $m^{th}$ (last) sample. For a model with a Wilcoxon $P(\epsilon_{extrap})<0.05$, the model does not extrapolate properly; and, it should be discarded. For a Wilcoxon $P(\epsilon_{extrap})>0.05$, the model is interesting, and higher P values correspond to models that are more plausible. The other error measure is precision. The precision for predicting concentration, CL and V is also measured as the standard deviation of extrapolated differences between the appropriate m and m−1 sample functions evaluated at the time of the $m^{th}$ sample.

Results: Table 2 lists the extrapolation error in C values for each of the five fit methods under comparison. Compared to $E_2$ SET and ordinary GV fitting, the extrapolation results of Tk-GV fitting are improved. Based on the Wilcoxon signed-ranks sum test, the $E_2$ SET model produces the largest error, significantly under-extrapolating with a probability of P=0.0046 that this error results from chance. More interestingly, the ordinary GV extrapolation has a Wilcoxon test probability of P=0.25. The $\beta \geq 0$ constrained GV fit has a 0.76 Wilcoxon probability of extrapolating correctly. The best extrapolation, from Tk-GV, has a Wilcoxon test probability of 0.91 of being correct. Hence, the Tk-GV method offers better assurance that AUC will be correctly estimated than by using the other methods listed in Table 2. Calculation of CL uses extrapolation of the concentration curve to infinity to find the AUC estimate. Since the Tk-GV method is able to extrapolate better than other methods, the Tk-GV method's value for CL should be more accurate as well.

TABLE 2

| Fit type | Wilcoxon test probability | Median difference[a] | Median difference 95% confidence limits |
|---|---|---|---|
| $E_2$ | 0.0046 | −0.0383 | −0.0634 to −0.0140 |
| $E_2$[b] | 0.0071 | −0.0373 | −0.0629 to −0.0118 |
| GV | 0.2446 | 0.0131 | −0.0088 to 0.0491 |
| GV[c] | 0.7638 | 0.0039 | −0.0158 to 0.0334 |
| Tk-GV | 0.9087 | −0.0011 | −0.0192 to 0.0217 |

Table 2 comments:
[a] From Wilcoxon signed-ranks sum. This does not always agree in sign with a sign difference.
[b] Constrained fit: $5 \geq \alpha \geq 0$, $2 \geq \beta \gamma \geq 0$ for $C(t) = K(\alpha e^{-\beta t} + e^{-\gamma t})$.
[c] Constrained fit: $\beta \geq 0$ for $C(t) = K t^{\alpha-1} e^{-\beta t}$.

TABLE 3

| | $CL_{m-1}$ | $CL_m$ | ΔCL Tk-GV | $s_{CL}$ | CV |
|---|---|---|---|---|---|
| mean | 74.99 | 74.47 | 0.52 | 3.90 | 8.96% |
| median | 74.73 | 74.28 | 0.46 | 2.65 | 5.05% |

TABLE 3-continued

| | $CL_{m-1}$ | $CL_m$ | ΔCL Tk-GV | $s_{CL}$ | CV |
|---|---|---|---|---|---|
| mean | 81.95 | 80.95 | 1.00 | 6.10 | 11.23% |
| median | 82.78 | 78.76 | 4.02 | 3.58 | 5.73% |

Table 3 comments:
ΔCL is the difference between the CL values calculated using (m − 1) and m samples; $s_{CL}$ is the standard deviation between each calculation; and CV is the coefficient of variation from using (m − 1) and m samples.

To understand the effects of extrapolative error better, CL values were calculated for the first (m−1) samples versus all m samples, and the effects on CL of extrapolation examined. Table 3 shows this for the Tk-GV model and for the constrained $E_2$ SET model, which provided the best SET-model performance. From Table 3, one can see that the benefit of waiting another 65 minutes after the next to last sample to take a last sample is to reduce the value of $CL_{Tk-GV}$ by about 0.5 ml/min and to reduce constrained $CL_{E2}$ by from 1 to 4 ml/min. Also note that the change in mean CL, i.e., the ΔCL values, the $s_{CL}$ (standard deviations of CL) and CV of CL are all improved for the Tk-GV model versus the constrained $E_2$ SET model. The $s_{CL}$, were pair-wise tested with Wilcoxon signed-ranks sum test for improvement in performance of the Tk-GV method as compared to constrained fits with an $E_2$ SET model. This showed that the precision of $CL_{Tk-GV}$ was significantly better than that of $CL_{E2}$ (P=0.0450, two-tailed). Another question is whether the 0.5 ml/min drop in $CL_{Tk-GV}$ from fits to m rather than m−1 samples is significant. The Wilcoxon signed-ranks sum test of the 46 paired differences is P=0.2273, two-tailed, or not significant. However, the same calculation for the constrained $CL_{E2}$ is significant (P=0.0049, two-tailed). $CL_{Tk-GV}$ was not significantly altered and constrained $CL_{E2}$ lost significant estimated CL by adding another period of an additional average of 65 minutes to take a last $8^{th}$ (or $9^{th}$) sample. Not shown in Table 3 are the V results for both models.

As calculated from the Tk-GV fit parameters, V was 16378±644 ml (mean±mean $s_V$) with a mean CV of 4.04%. For the constrained $E_2$ SET model, V was 15281±1589 ml with a mean CV of 9.49%. This suggests that use of the Tk-GV method represents a major increase in precision in the determination of V and that this reduction in V's CV is very significant (P=0.0014) as determined by a two-tailed Wilcoxon test. In sum, the Tk-GV model parameters were significantly less altered by varying the number of samples fit than constrained $E_2$ SET.

To verify the accuracy of the Tk-GV model, it was compared against the results from constant infusion of inulin and AUC with exponential extrapolation. This comparison was made using results described the literature.

Florijn et al. ("Glomerular filtration rate measurement by 'single-shot' injection of inulin." *Kidney Int* 46:252-252 (1994)) show that use of $E_2$ overestimates plasma clearance from constant infusion of inulin and that plasma clearance overestimates urinary clearance. Florijn et al.'s scaling of CL conversion between methods was done by the method of Du Bois and Du Bois ("A formula to estimate the approximate surface area if height and weight be known", *Arch Int Med* 17:863-871 (1916)): E (BSA)=$0.007184 W^{0.425} H^{0.725}$ in $m^2$, where W is patient mass in kg, and H is patient crown-heal height in cm, and the mks units of the 0.007184 coefficient are $28.18 \ m^{1.275}/k^{0.425}$. Florijn et al. give a 5.1 ml/min/1.73 $m^2$ greater $CL_{E2}$ than $CL_{total}$. The comparable number from the 46 studies here is 6.1 ml/min/1.73 $m^2$, with a 95% CI of 4.7 to 7.6 ml/min/1.73 $m^2$, see Table 4. From this, it can be seen that the $CL_{E2}$−$CL_{Tk-GV}$ value obtained using the inventive method is similar to Florijn et al.'s $CL_{E2}$–$CL_{total}$ result, in that the difference observed by Florijn et al.'s is within the Tk-GV CI. This leads to the reasonable conclusion that $CL_{Tk-GV}$ is a more accurate result than is $CL_{E2}$.

TABLE 4

| | Units | | | | |
|---|---|---|---|---|---|
| | ml/min/1.73 m² | | | Percent | |
| | Source | | | | |
| | Florijn et al. | | Moore et al. | | |
| | | | $E_2$ approximation | | |
| | 5 min injection[a] Constant infusion | Constrained[b] Tk-GV | 4 hour AUC[c] 24 hour | Constrained Tk-GV | |
| $CL_{total}$ method | infusion | 95% CI. | AUC | 95% CI. | |
| $CL_{E2} > CL_{total}$ | 5.1 | 6.1  4.7 to 7.6 | 10.0 | 10.6  8.6 to 12.7 | |
| $CL_{total} > CL_{urine}$ | 8.3 | ~7.3  — | 7.6 | ~7.0  — | |
| $CL_{E2} > CL_{urine}$ | 13.4 | —  — | 17.6 | —  — | |

Table 4 comments:
[a]inulin, $C_{obs}(t) \approx C(t) = k_1 e^{-\alpha(t-5)} + k_2 e^{-\beta(t-5)}$
[b]99mTc-DTPA, $C_{obs}(t) \approx C(t) = K(\alpha e^{-\beta t} + e^{-\gamma t})$ with constraints $0 \leq \alpha \leq 5$; $0 \leq \gamma \leq \beta \leq 2$.
[c]51Cr-EDTA, from numerical integration of $C_{obs}(t)$, then mono-exponential extrapolation.

The result of a test of the TK-GV method with Florijn et al.'s scaling methods, $$\frac{CL_{E2}}{BSA} = \frac{CL_{Tk-GV}}{BSA} + 6.1 \text{ ml/min/1.73 m}^2, \quad (15)$$

has a large standard error of estimation for CL of 5.0 ml/min/1.73 m² with $R^2 = 0.9869$. In order to verify the use of a mean difference between measurement systems, one should test that the measurements systems scale the same way. Therefore, a fit was performed yielding the regression result $CL_{E2}/BSA = 1.008 \, CL_{Tk-GV}/BSA + 5.564$ ml/min/1.73 m², where the 95% CI of the 1.008 slope is from 0.9734 to 1.043. The CI of slope includes one, so at least the two different CL-values scaled by BSA scale roughly in the same manner. However, upon further testing, the parameters (powers) of W and H of the BSA equation are not statistically warranted (P>0.1, ANOVA). This is expected as metabolism, not BSA, causes urine formation and BSA has a spurious correlation with CL. To calculate better scaling, one uses the mean $CL_{Tk-GV}$ value of 74.47 and the mean $\beta_{Tk-GV}$ value of 0.003614, and obtains $$CL_{E2} = 1.106 \cdot 74.47 \left( \frac{CL_{Tk-GV}}{74.47} \right)^{0.9972} \left( \frac{\beta_{Tk-GV}}{0.003614} \right)^{-0.1155} \text{ ml/min}, \quad (16)$$

which reduces the standard error of estimation to 4.2 ml/min., and increases the $R^2$ to 0.9919. Note that in Equation 16, the offset has been dropped as being probably no different from zero (0.1 ml/min, P(offset=0)=0.96, two-tailed t-test). Although a linear relationship with an offset approximates the relationship between $CL_{E2}$ and $CL_{Tk-GV}$ for Equation 15, the superior power function treatment (Equation 16) needs no offset. The power function is used because of more constant variance over the range, i.e., homoscedasticity, of the logarithms of CL-values than that of the CL-values, themselves. With the exception that one could set $CL_{Tk-GV}$'s 0.9972 exponent to one without much loss of precision, Equation 16's constants are significant. For example, the constant multiplier 1.106 has 95% CI's of 1.086 to 1.127. This suggests a 10.6% higher $CL_{E2}$ than weighted mean $CL_{Tk-GV}$ value. However, Equations 15 and 16 are imprecise because the $E_2$ SET renal elimination rate parameter is statistically unwarranted [P>0.05]. Using all samples and the $E_1$ SET model, one finds a better regression fit, $$CL_{E1} = \quad (17)$$
$$1.135 \cdot 74.47 \left( \frac{CL_{Tk-GV}}{74.47} \right)^{1.038} \left( \frac{\beta_{Tk-GV}}{0.003614} \right)^{-0.2102} + 5.967 \text{ ml/min},$$

where the standard error is 3.4 ml/min., and $R^2 = 0.9947$. An offset appears probable as P(offset=0)=0.005. Equation 17 does not fail ANOVA t-testing, and is more precise than Equations 15 and 16, which do fail ANOVA t-testing.

Figure 6:
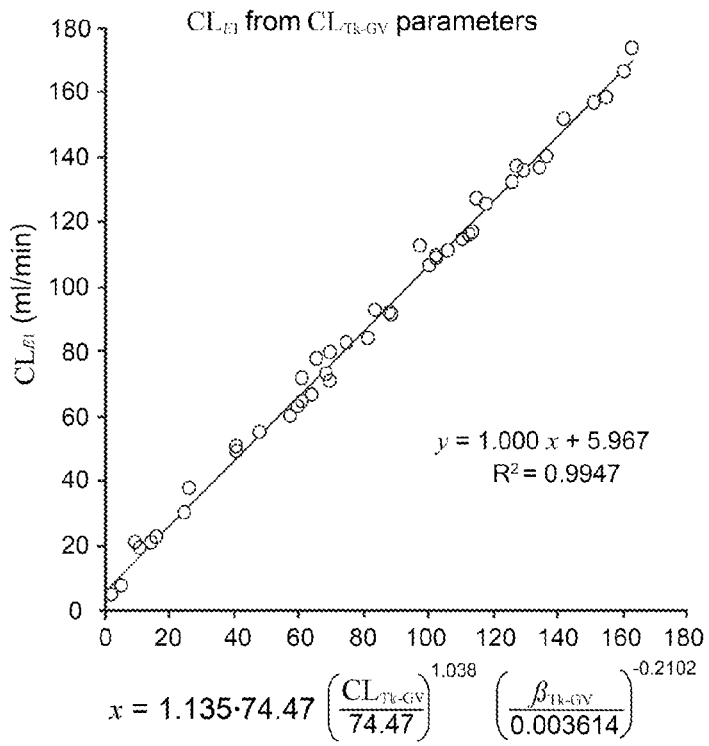
FIG. 6 is a plot of the result of regression of the mean scaled power function of Tk-GV parameters with offset to predict the $E_1$ SET plasma-clearance rate.

FIG. 6 shows the result of regression of the mean scaled power function of Tk-GV parameters with offset to predict $CL_{E1}$, the $E_1$ SET plasma-clearance rate. The Tk-GV parameters found to be statistically warranted were the plasma-clearance rate, $CL_{Tk-GV}$ and the renal-clearance rate constant, $\beta_{Tk-GV}$. The power function coefficient, 1.135 is dimensionless. The mean $CL_{Tk-GV}$ is 74.47 ml/min and provides the dimensions of x, with both powers and both ratios raised to those powers being dimensionless. Note how high the $R^2$ value is with only 0.53% of the variance being unexplained $(1-R^2)$.

When evaluating equations like Equations 15 through 18, the useful procedure for determining if an equation is posited correctly is to apply the ANOVA require-ment that the probability for each model's parameter(s) partial correlation coefficient achieves significance P<0.05 (like the P(offset=0)=0.005), above). When the same data is being used to regress similarly fitting but non-identical equations, parameters from those equations can be highly correlated. When comparing R-values or standard errors that are highly correlated parameters, apparently small differences can be significant. However, the probability of such a difference is irrelevant as it has no bearing on the ANOVA result.

The point is that although one can use a formula like Equation 15 to compare with published values, this is neither warranted (BSA and the offset are unwarranted, see Equation 16), nor precise (SE 5.0 versus 3.4 ml/min for Equation 18), and is not a recommended conversion formula. $CL_{E2}$ is best left discarded. If one has data enough to calculate a $CL_{E2}$ then the best conversion just calculates the more accurate and precise $CL_{Tk-GV}$ by using the inventive method for the same data.

The results of the above examples indicate a significant improvement in the relative precision of $V_{Tk-GV}$ compared to $V_{E2}$, (Wilcoxon P=0.0007, one-tailed). The increase in relative variance is 5.5-fold for V from $E_2$ SET versus Tk-GV, while the increase of variance of $CL_{E2}$ versus $CL_{Tk-GV}$ estimates is 1.6 fold. Thus, the Tk-GV model outperforms the constrained $E_2$ SET model by a significant margin. The Tk-GV model correctly estimates the CL and V values robustly, even when renal function is near zero. Even constant infusion cannot achieve this feat, as the infusion is problematic in renal failure. This gives confidence that the Tk-GV method and GV models for marker concentration have a physiological basis, even though some of the details are unknown.

The Tk-GV method can be used with a multitude of methods use for measuring drug or compound plasma concentration, for example, radioactive counting of radiolabeled markers, chemical assay, mass spectroscopy of various sorts, and so forth. The following list provides some of the techniques that may be used to give quantitative information on drug level.

(1) Immunoassay-based techniques (including various turbidometric/nephlometric techniques; Fluorescence Polarization Immunoassay (FPIA); Microparticle enhanced Immunoassay (MEIA); Cloned enzyme detection immunoassay (CEDIA), Enzyme multiplied immunoassay technique (EMIT), Time-resolved fluorescence immunoassay, Radioimmunoassay, Enzyme linked immunosorbent assay (ELISA)).

(2) Liquid Chromatography based techniques (including LC with UV and spectrophotometric detection; LC with single stage mass spectrometry or tandem mass spectrometry detection; LC with radioactivity detection).

(3) Gas Chromatography based techniques (including GC with Flame ionization detection; GC with Mass Spectrometric detection; and GC with tandem mass spectrometric detection).

(4) Radioactive assay with gamma (or beta) counting of radiolabeled markers, e.g., I-125 iodothalamate [16], $^{169}$Yb or $^{99m}$Tc-DTPA (diethylenetriamine penta-acetic acid) [17], 51Cr-EDTA (ethylenediamine tetra-acetic acid) [4] and a host of other radiolabeled drugs.

(5) Imaging data whether this is from computerized tomography of x-ray absorption of contrast agents or with assay of contrast, proton or other odd-mass-number nuclei nuclear magnetic resonance imaging with contrast or with assay of contrast, or gamma camera data with or without assay.

Other embodiments and modifications of the present invention will occur to those of ordinary skill in the art in view of these teachings. Accordingly, the invention is to be limited only the following claims which include all such other embodiments and modifications when viewed in conjunction with the above specification and accompanying drawings.

References (Incorporated Herein by Reference)

1. Masereeuw R, Russel F. Mechanisms and clinical implications of renal drug excretion. *Drug Metab Rev* 2001; 33:299-351.
2. Kinter W. Renal tubular transport of Diodrast-1131 and PAH in Necturus: evidence for simultaneous reabsorption and secretion. *Am J Physiol* 1959; 196:1141-1149.
3. Levitt D G. The pharmacokinetics of the interstitial space in humans. *BMC Clin Pharmacol* 2003; 3:3.
4. Chantler C, Barratt T M. Estimation of glomerular filtration rate from plasma clearance of 51-chromium edetic acid. *Arch Dis Child* 1972; 47:613-617.
5. Florijn K, Barendregt J, Lentjes E, Van Dam W, Prodjosudjadi W, van Saase J, et al. Glomerular filtration rate measurement by "single-shot" injection of inulin. *Kidney Int* 1994; 46:252-252.
6. Wise M E. Negative power functions of time in pharmacokinetics and their implications. *J Pharmacokinet Biopharm* 1985; 13:309-346.
7. Maisey M, Ogg C, Cameron J. Measuring glomerular filtration-rate. *Lancet* 1969; 1:733.
8. Schloerb P R. Total body water distribution of creatinine and urea in nephrectomized dogs. *Am J Physiol* 1960; 199:661-665.
9. Millard R K. Indicator-dilution dispersion models and cardiac output computing methods. *Am J Physiol* 1997; 272:H2004-2012.
10. Zierler K. A critique of compartmental analysis. *Annu Rev Biophys Bioeng* 1981; 10:531-562.
11. Larson K B, Cox J R. *Computer processing of dynamic images from an Anger scintillation camera: the proceedings of a workshop.* New York: Society of Nuclear Medicine; 1974
12. Moore A E, Park-Holohan S J, Blake G M, Fogelman I. Conventional measurements of GFR using 51 Cr-EDTA overestimate true renal clearance by 10 percent. *Eur J Nucl Med Mol Imaging* 2003; 30:4-8.
13. Calvert A H, Egorin M J. Carboplatin dosing formulae: gender bias and the use of creatinine-based methodologies. *Eur J Cancer* 2002; 38:11-16.
14. Fleming J S, Zivanovic M A, Blake G M, Burniston M, Cosgriff P S. Guidelines for the measurement of glomerular filtration rate using plasma sampling. *Nucl Med Commun* 2004; 25:759-769.
15. Piepsz A, Colarinha P, Gordon I, Hahn K, Olivier P, Sixt R, et al. Guidelines for glomerular filtration rate determination in children. *Eur J Nucl Med* 2001; 28:BP31-36.
16. Hall J, Guyton A, Farr B. A single-injection method for measuring glomerular filtration rate. *American Journal of Physiology—Renal Physiology* 1977; 232:72.
17. Russell C D, Bischoff P G, Kontzen F N, Rowell K L, Yester M V, Lloyd L K, et al. Measurement of glomerular filtration rate: single injection plasma clearance method without urine collection. *J Nucl Med* 1985; 26:1243-1247.
18. Stevens L, Coresh J, Greene T, Levey A. Assessing kidney function—measured and estimated glomerular filtration rate. *N Engl J Med* 2006; 354:2473.
19. Fux R, Biedermann T, Sander-Wiecker T, Morike K, Gleiter C, "Anaphylaxis to intravenous sinistrin", *The Annals of pharmacotherapy* 2004; 38:2175
20. Chandra R, Barron J, "Anaphylactic reaction to intravenous sinistrin (Inutest)", *Ann Clin Biochem* 2002; 39:76

The invention claimed is:

1. A method for estimating renal clearance rate of an injected exogenous compound in a patient, the method comprising:
   inputting a plurality of measured plasma concentration levels from patient samples taken at a plurality of time intervals after bolus injection of an exogenous compound into a computer processor programmed for executing an algorithm for:
   modeling plasma concentration in the patient samples using a gamma variate (GV) model according to the relationship $$C(t)=Kt^{\alpha-1}e^{-\beta t},$$

where K is a concentration scaling function, t is time, α is a shape parameter that is constrained to less than or equal to one, and β is the renal elimination rate constant where $$\lim_{\alpha \to 1} \beta \to 0;$$

using Tikhonov regularization to fit the modeled plasma concentration to temporal data, wherein using Tikhonov regularization includes applying a shrinkage factor λ so that the relative error in plasma clearance $s_{CL}$ within the relationship $$\left(\frac{s_{CL}}{CL}\right)^2 = s_\alpha^2(\bar{a}_1 + \ln\beta - \Psi(\alpha))^2 + s_\beta^2\left(\frac{\alpha}{\beta} - \bar{a}_2\right)^2 + 2s_{\alpha\beta}(\bar{a}_1 + \ln\beta - \Psi(\alpha))\left(\frac{\alpha}{\beta} - \bar{a}_2\right)$$

is minimized, where
Ψ(α) is the digamma function of α and Ψ(α)=d[lnΓ(α)]/dα=Γ'(α)/Γ(α);
generating an output comprising a display of the estimated plasma clearance for the patient.

2. The method of claim 1, wherein the one or more samples are blood samples.

3. The method of claim 1, wherein the one or more samples are images of contrast agents that were injected with the solution.

4. The method of claim 1, wherein the compound comprises a drug.

5. The method of claim 1, wherein the compound comprises a radiolabeled marker.

6. The method of claim 1, wherein the plurality of time intervals comprises at least three time points corresponding to an early time interval after injection, a late time interval after injection and a time interval between the early time interval and the late time interval.

7. The method of claim 1, wherein the plurality of time intervals comprises at least four time points corresponding to an early time interval after injection, a late time interval after injection and at least two additional time intervals between the early time interval and the late time interval.

8. A method for evaluating clearance of an injected exogenous compound in a patient, the method comprising:
inputting a plurality of measured plasma concentration levels from patient samples taken at a first time point and at least one second time point after injection of the exogenous compound into a memory of a computer having a processor programmed for executing an algorithm for:
modeling plasma concentration in the samples using a gamma variate (GV) model according to the relationship $$C(t) = K t^{\alpha-1} e^{-\beta t}$$

where K is a concentration scaling function, t is time, α is a shape parameter that is constrained to less than or equal to one, and β is the renal elimination rate constant where $$\lim_{\alpha \to 1} \beta \to 0;$$

using Tikhonov regularization to fit the modeled plasma concentration to temporal data, wherein using Tikhonov regularization includes applying a shrinkage factor λ so that the relative error in plasma clearance $s_{CL}$ within the relationship $$\left(\frac{s_{CL}}{CL}\right)^2 = s_\alpha^2(\bar{a}_1 + \ln\beta - \Psi(\alpha))^2 + s_\beta^2\left(\frac{\alpha}{\beta} - \bar{a}_2\right)^2 + 2s_{\alpha\beta}(\bar{a}_1 + \ln\beta - \Psi(\alpha))\left(\frac{\alpha}{\beta} - \bar{a}_2\right)$$

is minimized, where
Ψ(α) is the digamma function of α and Ψ(α)=d[lnΓ(α)]/dα=Γ'(α)/Γ(α);
generating an output in the memory comprising a calculated value for the plasma clearance for the patient; and
transferring the output from the memory to a non-transitory computer-readable media.

9. The method of claim 8, wherein the sample is a blood sample.

10. The method of claim 8, wherein the sample is an image of contrast agents that were injected with the solution.

11. The method of claim 8, wherein the compound comprises a drug.

12. The method of claim 8, wherein the compound comprises a radiolabeled marker.

13. The method of claim 8, wherein the at least one second timepoint comprises at least two different time points after injection.

14. The method of claim 8, wherein the at least one second timepoint comprises at least three different time points after injection.

15. A method for evaluating clearance of an exogenous compound injected into a patient, the method comprising:
measuring plasma concentration of the compound in each of a plurality of samples collected from the patient, wherein said measuring is performed at time intervals ranging from about five minutes to about twenty-four hours;
inputting the measured plasma concentration into a memory of a computer having a processor programmed for executing an algorithm for:
inputting a plurality of measured plasma concentration levels from the samples into a memory of a computer having a processor programmed for executing an algorithm for:
modeling plasma concentration in the samples using a gamma variate (GV) model according to the relationship $$C(t) = K t^{\alpha-1} e^{-\beta t}$$

where K is a concentration scaling function, t is time, α is a shape parameter that is constrained to less than or equal to one, and β is the renal elimination rate constant where $$\lim_{\alpha \to 1} \beta \to 0;$$

using Tikhonov regularization to fit the modeled plasma concentration to temporal data, wherein using Tikhonov regularization includes applying a shrinkage factor λ so that the relative error in plasma clearance $s_{CL}$ within the relationship $$\left(\frac{s_{CL}}{CL}\right)^2 = s_\alpha^2(\bar{a}_1 + \ln\beta - \Psi(\alpha))^2 + s_\beta^2\left(\frac{\alpha}{\beta} - \bar{a}_2\right)^2 + 2s_{\alpha\beta}(\bar{a}_1 + \ln\beta - \Psi(\alpha))\left(\frac{\alpha}{\beta} - \bar{a}_2\right)$$

is minimized, where
$\Psi(\alpha)$ is the digamma function of $\alpha$ and $\Psi(\alpha) = d[\ln\Gamma(\alpha)]/d\alpha = \Gamma'(\alpha)/\Gamma(\alpha)$;

generating an output in the memory comprising a calculated value for the plasma clearance for the patient; and
transferring the output from the memory to a non-transitory computer-readable media.

* * * * *